United States Patent [19]

Madden et al.

[11] Patent Number: 5,244,464
[45] Date of Patent: Sep. 14, 1993

[54] BAND FOR SECURING AND ALIGNING MEDICAL TUBING

[76] Inventors: Diane T. Madden, Carmel, Ind.; Judith H. Ellers, 1508 Coleman St., Wilmington, Del. 19805; Dennis Madden, 686 Woodbine Dr., Carmel, Ind. 46032, executor of said Diane T. Madden, deceased

[21] Appl. No.: 901,927

[22] Filed: Jun. 22, 1992

[51] Int. Cl.$^5$ .................................. A61M 25/02
[52] U.S. Cl. .......................... 604/179; 128/DIG. 6
[58] Field of Search ............... 604/174, 179, 180; 129/DIG. 28, DIG. 6

[56] References Cited

U.S. PATENT DOCUMENTS

| | | | |
|---|---|---|---|
| 3,726,280 | 4/1973 | Lacount | 604/179 |
| 3,878,849 | 4/1975 | Muller et al. | 604/179 |
| 4,018,221 | 4/1977 | Rennie . | |
| 4,088,136 | 5/1972 | Hasslinger et al. | 128/DIG. 26 |
| 4,096,863 | 6/1978 | Kaplan et al. . | |
| 4,273,130 | 6/1981 | Simpson . | |
| 4,445,894 | 5/1984 | Kovacs . | |
| 4,548,200 | 10/1985 | Wapner . | |
| 4,569,348 | 2/1986 | Hasslinger . | |
| 4,574,798 | 3/1986 | Heitzman . | |
| 4,591,356 | 5/1986 | Christie | 128/DIG. 26 |
| 4,610,245 | 9/1986 | Biearman | 128/DIG. 26 |
| 4,665,566 | 5/1987 | Garrow . | |
| 4,739,757 | 4/1988 | Edwards | 128/DIG. 26 |
| 4,774,946 | 10/1988 | Ackerman et al. | 128/DIG. 26 |
| 4,799,923 | 1/1989 | Campbell | 604/179 |
| 4,966,590 | 10/1990 | Kalt | 604/180 |
| 4,988,338 | 1/1991 | Taylor et al. | 604/180 |

*Primary Examiner*—Paul J. Hirsch
*Attorney, Agent, or Firm*—Woodard, Emhardt, Naughton, Moriarty & McNett

[57] ABSTRACT

A band for securing and aligning medical tubing relative a portion of a human body is disclosed including primary and secondary straps constructed of VELFOAM ®. The primary strap includes a male VELCRO ® portion fastened to the foam substrate of the VELFOAM ® so that the primary strap can be adjustably fastened to itself about a portion of a human body. The secondary strap includes one or more male VELCRO ® portions attached to the foam substrate of the VELFOAM ®. The secondary strap attaches at its ends anywhere along the primary strap, trapping the medical tubing between its ends and the primary strap to secure the medical tubing in place.

12 Claims, 8 Drawing Sheets

BAND FOR SECURING AND ALIGNING MEDICAL TUBING

BACKGROUND OF THE INVENTION

This invention relates generally to medical device support equipment and more specifically to a band for securing and aligning a tubular medical device relative a portion of a human body.

Frequently, convalescing patients require continuous medical treatment such as that provided by medical devices assisting with respiration, medication, monitoring and/or drainage of bodily fluids of the patient. These medical devices typically require lengths of medical tubing, such as catheters, ventilators, electrical leads and the like, attached between the patient and a base unit to provide treatment. Because the medical tubing must be maintained in a relatively fixed position on the patient for extended periods of time, it is desirable to attach the tubing to the patient to accommodate movement of the patient without disturbing the attachment of the tubing.

Oftentimes, for lack of a fully versatile band, the medical tubing is attached by taping the tubing down against the patient's skin or clothing. Clearly, tape is the least desirable choice for securing and aligning medical tubing relative a patient, since patient excretions such as perspiration, blood or saliva can wet the tape, causing it to loosen and the medical tubing to become dislodged. As a result, there are presently a number of devices available for securing catheters and the like to a person's limb.

For example Kovacs, U.S. Pat. No. 4,445,894, provides a band for securing a catheter to a limb comprising a stretchable primary strap adapted to encircle the limb, and a secondary strap fixedly attached to the primary strap. The exposed surface of the primary strap adjacent the secondary strap is made of a soft, looped fabric and the outwardly facing surface of the secondary strap is made of a male VELCRO ®-type fastening material, wherein the secondary strap is designed to be looped over and encircle the catheter and connect with the looped fabric of the primary strap to hold the catheter securely in place. Although perhaps an improvement over merely taping the catheter to the patient's skin or clothing, the device by Kovacs does not offer the same versatility as that provided by taping. Instead, the device by Kovacs predetermines the precise location of the attachment of the tubing to the band by fixing the location of the secondary strap relative the primary strap. Therefore, the primary strap must be re-positioned to adjust the orientation of the tubing relative the limb.

Similarly, the catheter tube holder strap provided by Hasslinger, U.S. Pat. No. 4,569,348, describes primary strap sections which encircle a limb, and a secondary flexible strap section which loops about and adheres to itself and to the surface of a catheter tube. The secondary flexible strap section is adapted to be placed in selective detachable engagement with the surface of the primary strap section, wherein the primary strap section attaches to itself over and around the secondary strap section, fully encompassing the catheter tube and secondary strap section for support. As such, Hasslinger also does not provide the versatility which is afforded by merely taping the catheter as required to the patient's skin and clothing. Instead, Hasslinger also limits the placement of the catheter relative the holder strap by requiring the primary strap section to overlap the secondary flexible strap section to support the catheter tube. As a result, the catheter must be located near the overlapping region of the primary strap section to be secured properly. Other straps and bands for anchoring medical tubing which also fix a secondary or catheter holding strap relative a primary strap are discussed in Kaplan et al., U.S. Pat. No. 4,096,863 and Garrow, U.S. Pat. No. 4,665,566.

One specific example demonstrating a need for a more versatile medical tubing support device is the respiratory tubing associated with tracheotomy patients. Previous appliances for supporting respiratory tubing adjacent a patient's chest or back portion have employed a plate-like base contoured to lie upon a patient's chest or corresponding back portion. See, for example, Heitzman, U.S. Pat. No. 4,574,798. In such an application, the variation in size of the torso of patients is considerably greater than the variation in limb size. Also, the location of the respiratory tubing must be more precisely controlled to prevent spasms or normal movements of the patient from causing the life-sustaining respiratory equipment to be displaced. Therefore, it is highly desirable to provide a medical tubing support device which is easily adjusted to properly secure and align medical tubing relative a patient's torso.

A need therefore exists for an improved band which both secures and aligns a tubular medical device adjacent a portion of a human body. Such a band should be tape-free to avoid the many problems associated with taping tubular medical devices to a patient's skin or clothing, while still providing the attachment versatility of tape. Also, such a device should securely affix the medical tubing relative a patient's body to discourage self or accidental removal and disconnection of the medical tubing, and to prevent irritation and gouging caused by movement of the medical tubing relative the patient. Such a device should be comfortable to the patient and provide cushioning between the tubing and the patient. Therefore, the device should be without metallic mechanical attachments, such as metal hooks and buttons.

Further, such a device should be conveniently and efficiently manipulated to secure and align medical tubing relative the patient, without requiring disconnection of the medical tubing for use with the device and without semi-permanently attaching the device to the medical tubing. Preferably, such a device should be infinitely adjustable both with respect to the secure mounting of the band to the patient and the secure mounting of the tubular medical device to the band. Most importantly, such a device should permit the adjustment of the location of the tubing relative the primary strap without a re-positioning or otherwise affecting the primary strap. Ideally, such a device would resist the lavaging of accumulated moisture and degradation. Regardless, such a device should be simple to manufacture so that it may be economically and sanitarily discarded after use.

SUMMARY OF THE INVENTION

One embodiment of this invention might include a band for securing and aligning medical tubing relative a portion of a human body. The band includes a first strap having a hook and loop engaging outer layer for receiving hook and loop attachments thereon and means for adjustably fastening the first strap about a portion of a human body. A detachable second strap is also provided which is adjustably attachable along the hook and loop engaging outer layer of the first strap. The second strap has a hook and loop engaging inner layer corresponding to the hook and loop engaging outer layer of the first strap for attaching to the first strap at ends of the second strap. The second strap attaches to the first strap across a portion of the medical tubing to secure and align the medical tubing against the first strap between the ends of the second strap.

One object of the present invention is to provide an improved band which both secures and aligns medical tubing adjacent a portion of a human body.

Another object of the present invention is to provide a band which is adhesive-free to avoid the many problems associated with taping medical tubing to a patient's skin or clothing, while still providing the attachment versatility of tape.

Yet another object of the present invention is to provide a band which securely affixes medical tubing relative a patient's body to discourage self or accidental removal and disconnection of the medical tubing, and to prevent irritation and gouging caused by movement of the medical tubing relative the patient.

Still yet another object of the present invention is to provide a band which is comfortable to the patient and provides cushioning between the tubing and the patient.

Still another object of the present invention is to provide a band void of metallic mechanical attachments, such as metal hooks and buttons.

Yet another object of the present invention is to provide a band which is conveniently and efficiently manipulated to secure and align medical tubing relative the patient, without device and without semi-permanently attaching the device to the medical tubing.

Still yet another object of the present invention is to provide a band which is infinitely adjustable both with respect to the secure mounting of the band to the patient and the secure mounting of the tubular medical device to the band.

Still another object of the present invention is to provide a band which permits the adjustment of the location of the tubing relative the primary strap without re-positioning or otherwise affecting the primary strap.

Still yet another object of the present invention is to provide a band which resists accidental lavaging of accumulated moisture and degradation and is simple to manufacture so that it may be economically and sanitarily discarded after use.

These and other related objects and advantages of the present invention are described further in the following drawings and written description.

DESCRIPTION OF THE PREFERRED EMBODIMENT

Figure 1:
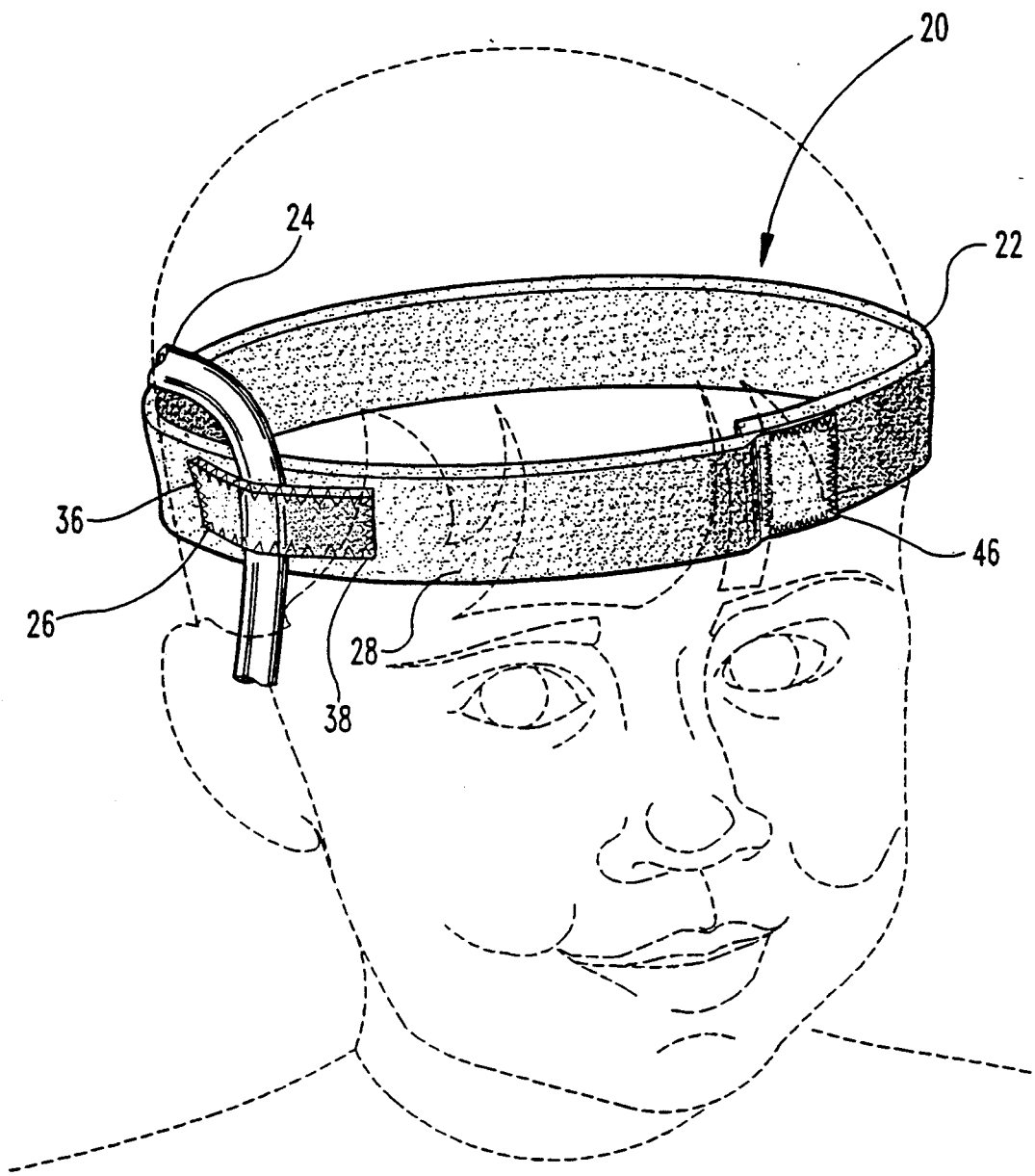
FIG. 1 is a perspective view of a band for securing and aligning a tubular medical device according to one embodiment of the present invention adapted for securing a portion of medical tubing, such as drainage tubing, relative a patient's head.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to FIG. 1, a band 20 for securing and aligning medical tubing, such as drainage tubing, is shown fastened about a patient's head. Band 20 includes a primary strap 22 employing hook and loop means, such as VELCRO®, for adjustably fastening to itself to secure band 20 to the head. Band 20 further provides means for detachably securing and aligning drainage tubing 24 to strap 22 via secondary strap 26. The surface of outer layer 28 of primary strap 22 is covered with loop-type filamentary engaging elements adapted for forming a hook and loop attachment when engaged with corresponding hook-type engaging elements.

The inner layer surface of secondary strap 26 is covered with hook-type engaging elements corresponding to the loop-type filamentary engaging elements of the primary strap. As such, when secondary strap 26 is brought into contact with primary strap 22, the hook-type engaging elements of the secondary strap intermesh with the loop-type filamentary engaging elements of the primary strap to form hook and loop attachments at ends 36 and 38 of secondary strap 26, thereby trapping tubing 24 between ends 36 and 38 against the primary strap to securely hold tubing 24 in place. Further, primary strap 22 and secondary strap 26 are of sufficient width so as to effectively align medical tubing 24 relative primary strap 22.

Figure 2:
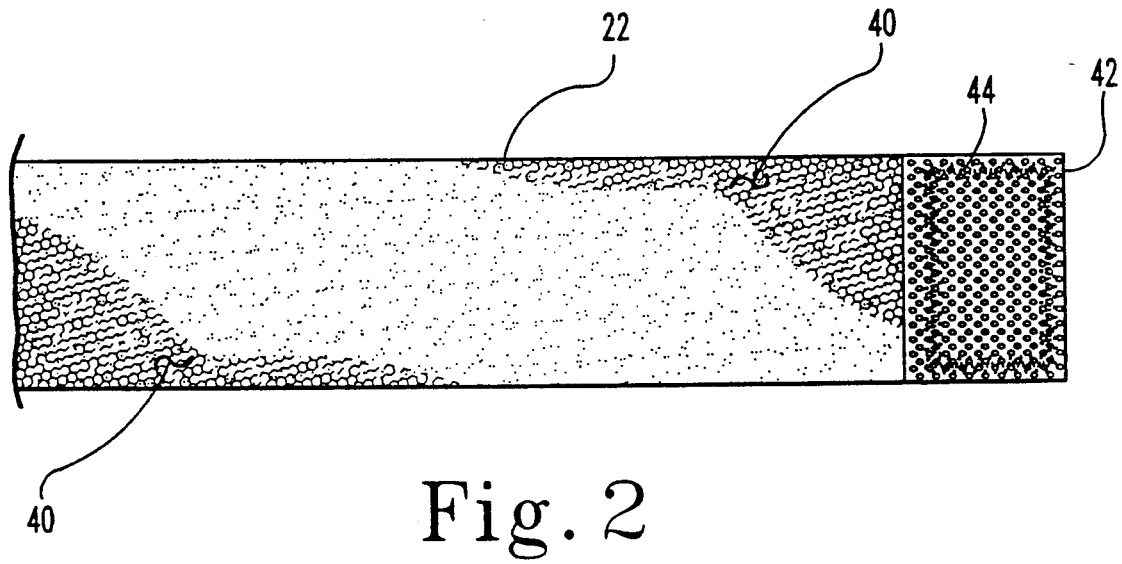
FIG. 2 is a bottom plan view of a primary strap of the band shown in FIG. 1.
Figure 3:
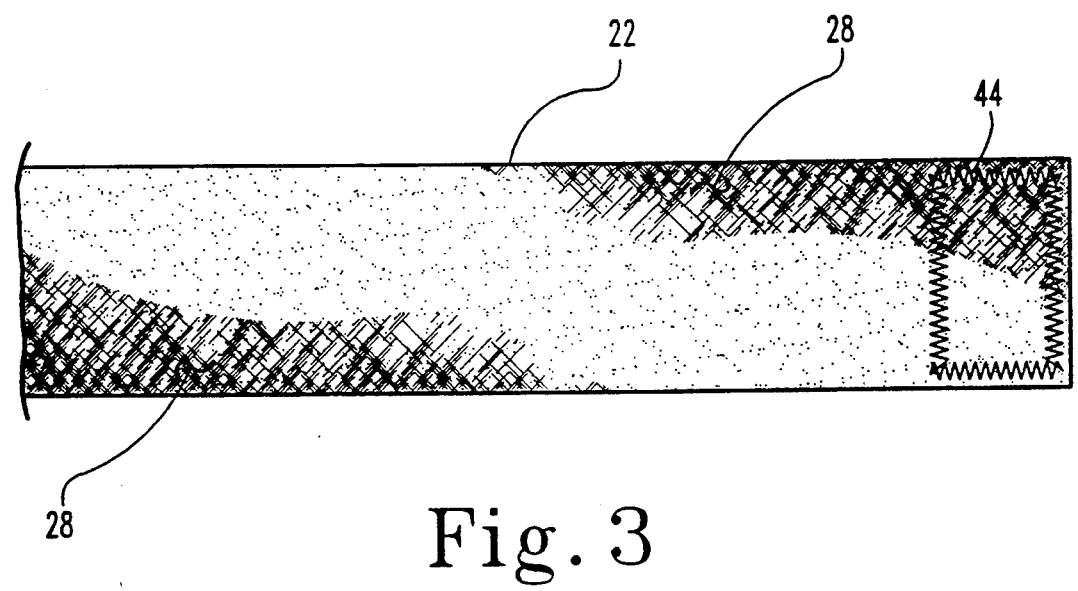
FIG. 3 is a top plan view of the primary strap of the band shown in FIG. 1.

Referring now to FIGS. 2 and 3, the construction of primary strap 22 is shown in greater detail. In FIG. 2, the inner layer 40 is shown extending across the length of primary strap 22. Inner layer 40 is constructed of hypoallergenic foam to provide cushioning for patient comfort, and is adhered to outer layer 28 of primary strap 22. A hook-type engaging portion 42 is fastened to the foam inner layer 40 via stitching 44, wherein stitching 44 compresses the foam between outer layer 28 and hook-type engaging portion 42 to define a reduced thickness handling portion 46 (see FIG. 1). In addition to providing a soft, resilient surface for minimizing localized pressure applied to the patient, foam inner layer 40 also provides resilient gripping means for preventing undesirable movement of the band when in place secured against the patient's head.

Referring now to FIG. 3, outer layer 28 is also shown extending across the length of primary strap 22. Outer layer 28 is constructed of a textile material having a multiplicity of loop-type filamentary engaging elements. As such, secondary strap 26 can be attached anywhere along outer layer 28, including reduced thickness portion 46, to provide a fully versatile band 20. In the preferred embodiment, primary strap 22 is constructed of VELFOAM ®, a soft flexible material with a foam substrate adhered to a cotton-lined backing. Hook-type engaging portion 42 is constructed of male VELCRO ® and, therefore, has a plurality of upstanding hooks which engage the woven or looped fabric of the VELFOAM ® cotton-lined backing to form a tight hook and loop attachment.

Primary strap 22 is contemplated having one or more standard lengths, wherein in use primary strap 22 can be cut to length at the end opposite hook-type engaging portion 42 to tailor strap 22 to the individual needs of the patient. As such, band 20 provides a "one size fits all" capability to simplify its availability and application, and to reduce inventory control and cost. Nevertheless, in the preferred embodiment two basic sizes are provided for band 20 to reduce the amount of wasted material and, ultimately, reduce cost to the patient. A "neo-natal" size is provided for babies and other small children, and an "adult" size is provided for older children ranging up to adults. Extra-width versions are also contemplated for especially large patients to provide additional cushioning and comfort.

Figure 4:
FIG. 4 is a top plan view of a secondary strap of the band shown in FIG. 1.
Figure 5:
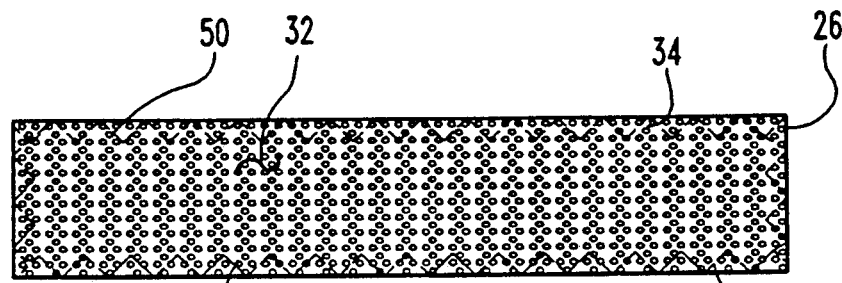
FIG. 5 is a bottom plan view of the secondary strap of the band shown in FIG. 1.

Referring now to FIGS. 4 and 5, secondary strap 26 is shown in greater detail. In FIG. 5, the surface of inner layer 32 is shown covered with hook-type engaging elements 34. Outer layer 48 of secondary strap 26 can be constructed of a variety of flexible backing materials; however, in the preferred embodiment, secondary strap 26 is constructed of VELFOAM ® similar to primary strap 22. As such, outer layer 48 comprises the cotton-lined backing layer of VELFOAM ® and has a foam substrate adhered thereto. Hook-type engaging elements 34 are provided for inner layer 32 by fastening a length of male VELCRO ® to the foam layer of the VELFOAM ®, as provided by stitching 50 indicated in FIGS. 4 and 5.

Similar to primary strap 22, secondary strap 26 is constructed employing a "one size fits all" philosophy. Two standard sizes are provided corresponding to the neo-natal and adult standard sizes of the primary strap. For example, band 20 in the neo-natal size employs a primary strap 22 which is 15 inches (0.381 m) long and 2 inches (0.051 m) wide, wherein male VELCRO ® portion 42 is 1 inch (0.025 m) in length. Secondary strap 26 in the neo-natal size has a corresponding length of 5 inches (0.127 m) and width of 1 inch (0.025 m). In the adult size, primary strap 22 has a length of 55 inches (1.397 m) and a width of 2 inches (0.051 m), wherein male VELCRO ® portion 42 is 2 inches (0.051 m) long. Secondary strap 26 in the adult size has a length of 7 inches (0.178 m) and a width of 1 inch (0.025 m). As previous discussed, for especially large patients the width of primary strap 22 and secondary strap 26 may be doubled for added comfort.

Figure 6:
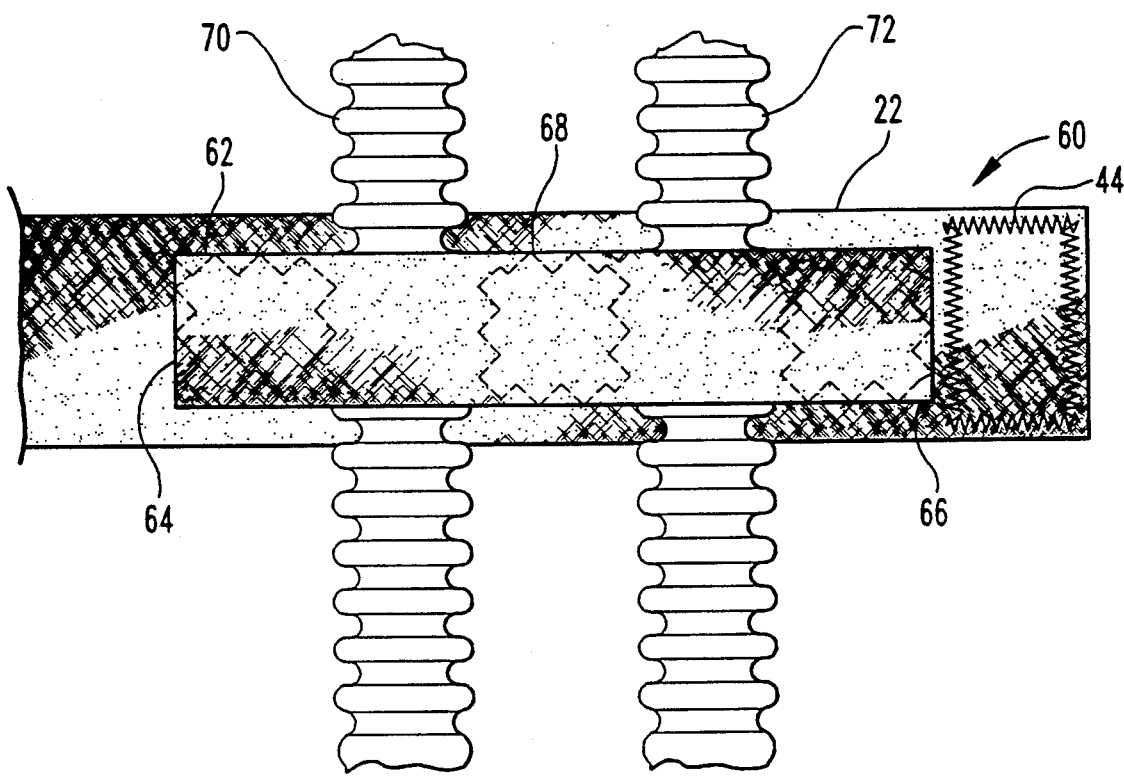
FIG. 6 is a top plan view of a band for securing and aligning a tubular medical device according to another embodiment of the present invention adapted for securing multiple medical tubing portions, such as respiratory tubing.

Referring now to FIG. 6, an alternate embodiment of a band for securing and aligning medical tubing, such as respiratory tubing, is shown. Band 60 includes a primary strap 22 like that of band 20. However, to accommodate multiple portions of medical tubing, band 60 includes a secondary strap 62 which, in addition to attaching to primary strap 22 at ends 64 and 66 thereof, also attaches to primary strap 22 at a middle portion 68. As such, in this embodiment medical tubing 70 and 72 are each individually secured and aligned relative primary strap 22 by a common secondary strap.

Figure 7:
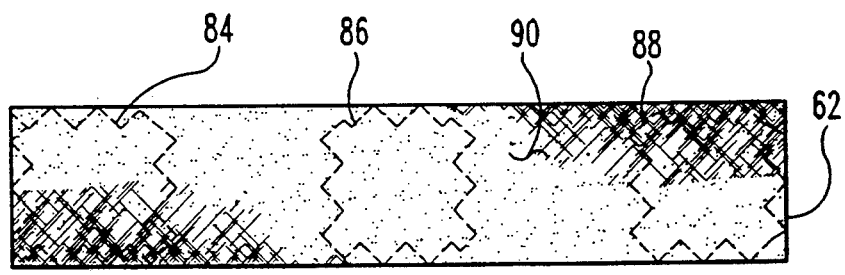
FIG. 7 is a top plan view of a secondary strap of the band shown in FIG. 6.
Figure 8:
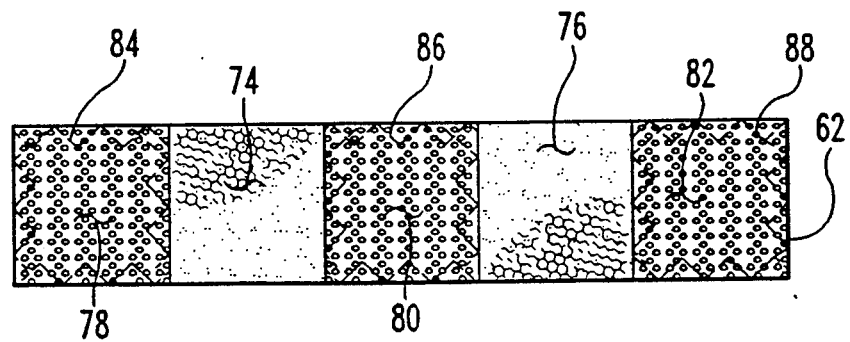
FIG. 8 is a bottom plan view of the secondary strap of the band shown in FIG. 6.

Referring now to FIGS. 7 and 8, the construction of secondary strap 62 is shown in greater detail. Similar to secondary strap 26, secondary strap 62 is constructed of VELFOAM ®. In FIG. 8, the foam substrate of the VELFOAM ® is exposed at portions 74 and 76, each of which correspond to the medical tubing portions 70 and 72, respectively, of FIG. 6. Portions 74 and 76, therefore, provide resilient gripping means tending to maintain the medical tubing in fixed relation to primary strap 22. Male VELCRO ® portions 78, 80 and 82 are each fastened to the VELFOAM ® material by corresponding stitchings 84, 86 and 88. Referring now to FIG. 7, cotton-lined backing layer 90 is shown extending the length of secondary strap 62 with the VELCRO ® stitchings 84, 86, and 88 shown extending therethrough. In the preferred embodiment, male VELCRO ® portions 78, 80, and 82 are each 1 inch (0.025 m) in length and are fastened to secondary strap 26 equidistant from each other.

Figure 9:
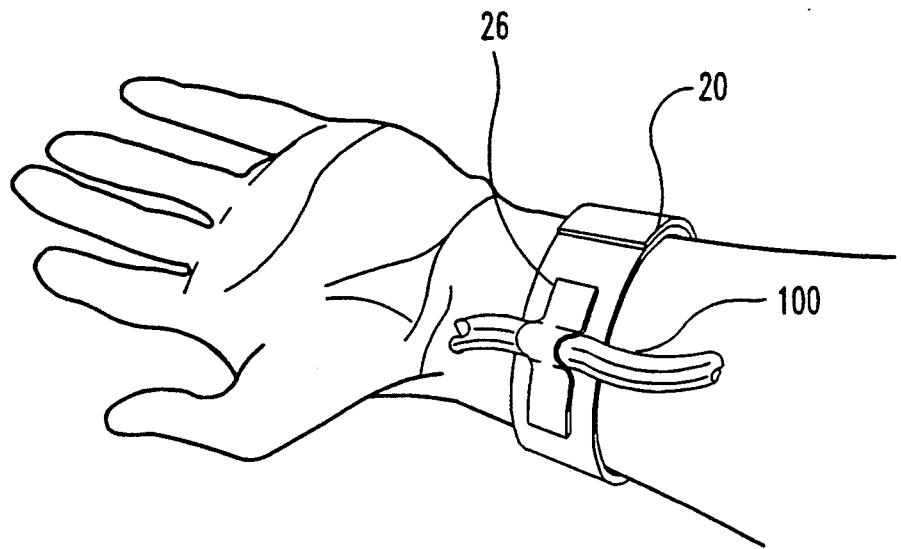
FIG. 9 is a perspective view of the band of FIG. 1 adapted for securing and aligning medical tubing, such as intravenous tubing, relative to a patient's hand.
Figure 10:
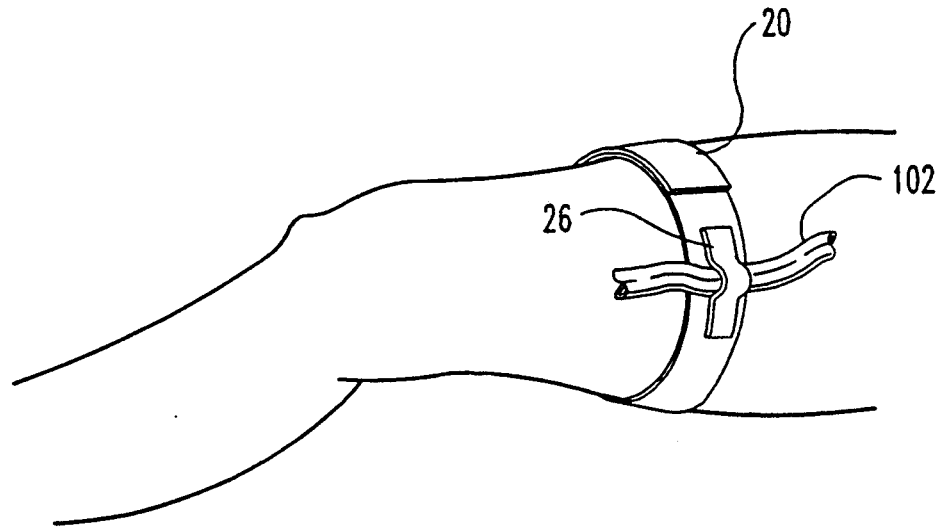
FIG. 10 is a perspective view of the band of FIG. 1 adapted for securing and aligning medical tubing, such as a catheter, relative to a patient's leg.

Referring now to FIG. 9, band 20 is shown fastened about a patient's wrist with secondary strap 26 securing and aligning medical tubing, such as intravenous tubing 100, relative thereto. Similarly, in FIG. 10 band 20 is shown fastened about a patient's thigh with secondary strap 26 securing and aligning medical tubing, such as a catheter 100 of a percutaneous insertion system. In the embodiments shown in FIGS. 9 and 10, band 20 is cut to the appropriate length to wrap around the limb and onto itself. Because the outer layer 28 of band 22 encircles the limb, secondary strap 26 can be secured anywhere along band 22, including onto its overlapping regions. Further, band 20 is not limited to fastening about limbs of a body, but instead can be adapted for securing about a torso in a harness-like fashion.

Figure 11:
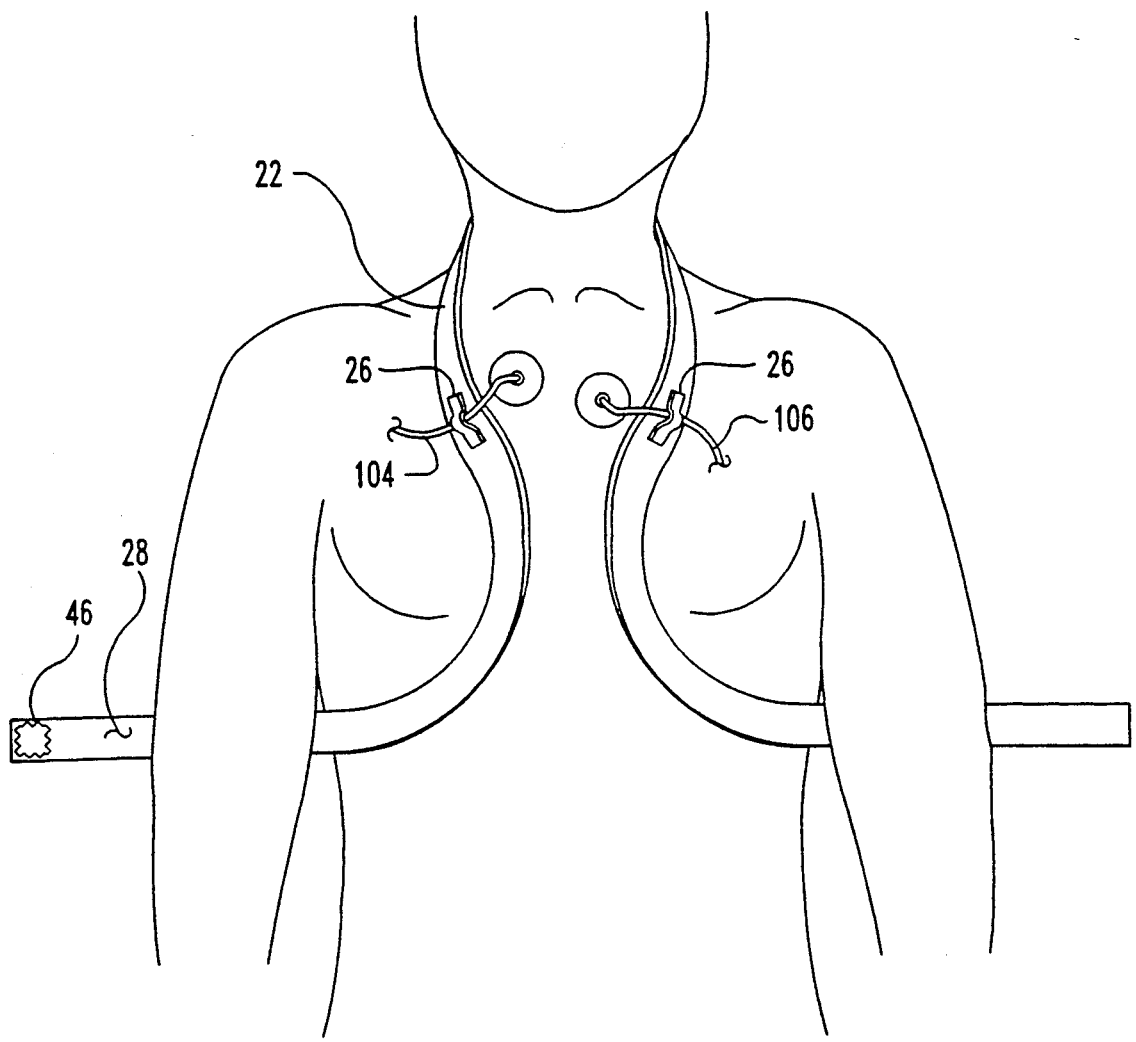
FIG. 11 is a front elevational view of the band shown in FIG. 1 adapted for securing and aligning medical tubing, such as EKG sensor electrical leads, in a harness-like fashion relative a patient's torso.
Figure 12:
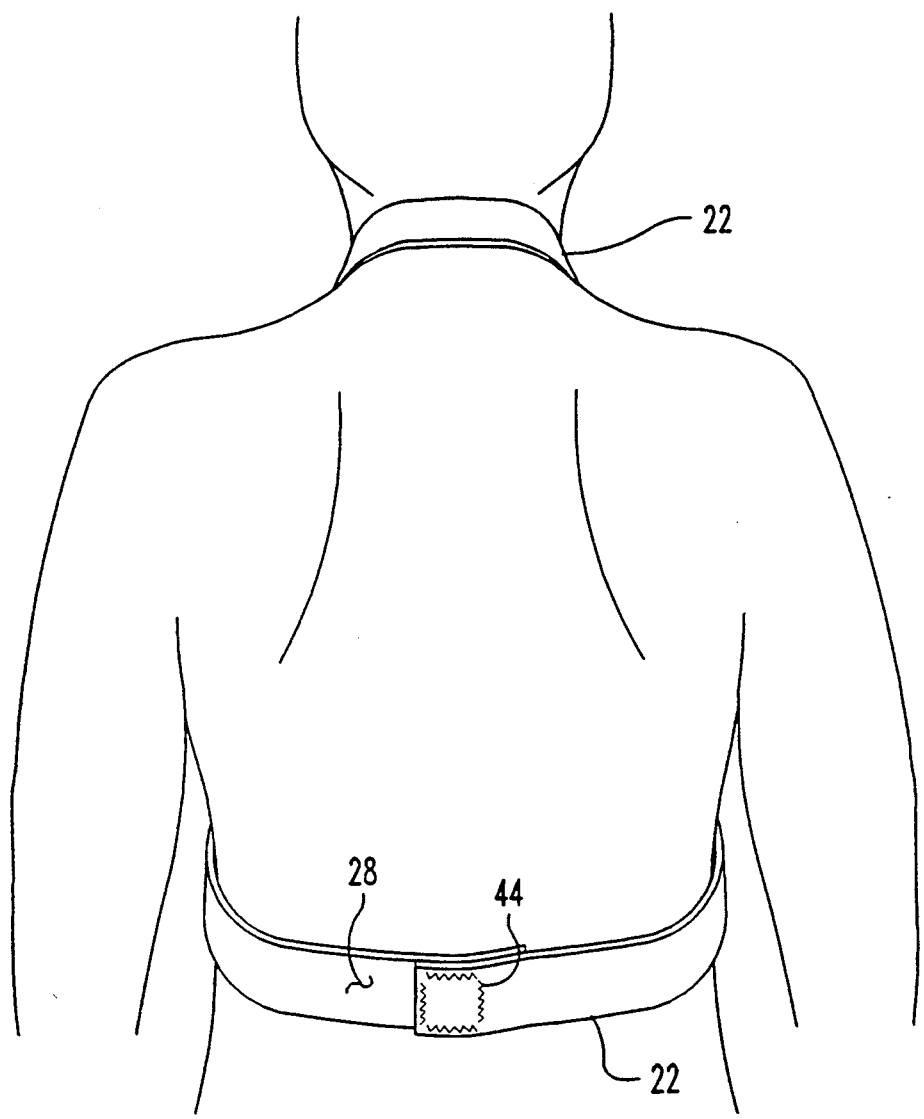
FIG. 12 is a rear elevational view of the band of FIG. 11 secured relative to the patient's torso.

Referring now to FIGS. 11 and 12, primary strap 22 is shown in partial assembly adjacent a patient's torso, wherein strap 22 is wrapped around the neck and shoulders and underneath each arm. One or more portions of medical tubing, such as electrocardiogram leads 104 and 106, can be fastened along the outer layer 28 of strap 22 as required to locate and prevent entanglement of the leads. In FIG. 12, primary strap 22 is shown adjustably fastened to and overlapping itself to securely position the harnessed strap in place. Because the outer layer 28 of primary strap 22 incorporates means for hook and loop engagement along its entire length, medical tubing can be secured and aligned relative primary strap 22 in a variety of locations corresponding to the patient's torso, thus rendering near tape-like versatility.

Figure 13:
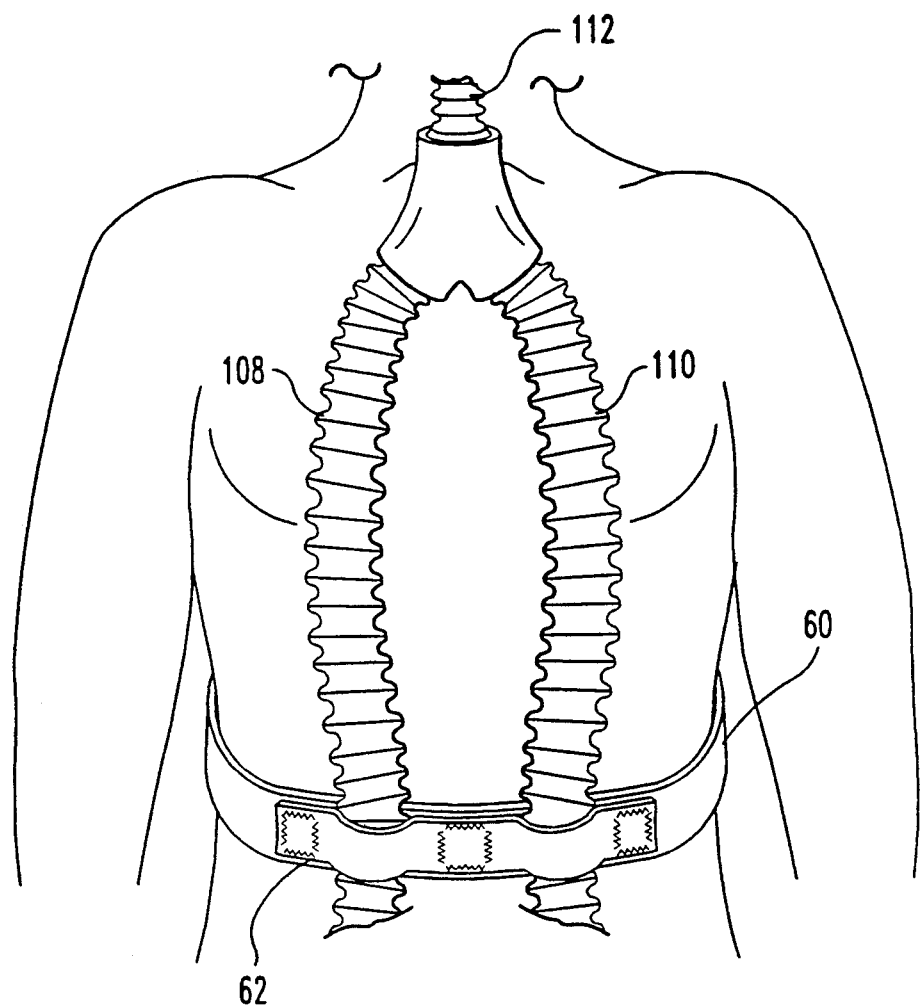
FIG. 13 is a front plan view of the band shown in FIG. 6 adapted for securing and aligning medical tubing, such as tracheotomy tubing, relative a patient's torso.

Referring to FIG. 13, band 60 is shown secured about a patient's torso with secondary strap 62 securing and aligning tracheotomy tubing 108 and 110 relative a tracheotomy patient. Band 60 provides extra comfort to the tracheotomy patient by preventing "pull" caused by the patient's movements relative the respiratory tubing and, therefore, minimizes the risk of the patient developing mucousal and/or tracheal irritation.

Additionally, band 60 does not directly secure the endotracheal tube 112 at the airway. Rather, band 60 secures the tubing 108 and 110 connected to the endotracheal tube 112. Other applications contemplated for band 20 or band 60, or a combination thereof include, but are not limited to, securing and aligning various forms of chest tubes and gastrostomy tubes. Regardless of the specific application, the bands embodied herein prevent accidental and often life-threatening extubation or decannulation of the tubing by providing a versatile band which can be optimally situated to properly secure the tubing.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A band for use securing and aligning medical tubing relative a portion of a human body, comprising:
   a first strap having a hook and loop engaging outer layer for receiving hook and loop attachments thereon;
   means for adjustably fastening said first strap about a portion of a human body; and
   a detachable second strap adjustably attachable along the hook and loop engaging outer layer of said first strap;
   said second strap having a hook and loop engaging inner layer corresponding to said hook and loop engaging outer layer of said first strap for attaching to said first strap at ends of said second strap, said hook and loop engaging inner layer being attached to a foam substrate;
   said second strap being adapted to attach to said first strap across a portion of the medical tubing to secure and align the medical tubing against said first strap between said ends of said second strap.

2. The band of claim 1, wherein:
   said second strap includes a cotton-lined backing layer adhered to said foam substrate.

3. The band of claim 2, wherein:
   said hook and loop engaging inner layer is comprised of hook and loop engaging inner layer end portions fastened to said foam substrate at said ends of said second strap; and
   said second strap attaches to said first strap at said hook and loop engaging inner layer end portions, a portion of said foam substrate being exposed between said hook and loop engaging inner layer end portions and adapted for contacting and gripping across the medical tubing to further secure and align the medical tubing.

4. The band of claim 3, wherein:
   said second strap includes a third hook and loop engaging inner layer portion fastened to said foam substrate between said hook and loop engaging inner layer end portions of said second strap; and
   said second strap being adapted to attach to said first strap at said third hook and loop engaging inner layer portion and across two medical tubing portions, one medical tubing portion being adapted to be secured between one of said ends of said second strap and said third hook and loop engaging inner layer portion, and the other medical tubing portion being adapted to be secured between said other end of said second strap and said third hook and loop engaging inner layer portion.

5. The band of claim 4, wherein:
   said hook and loop engaging outer layer of said first strap comprises loop-type filamentary engaging elements adapted for forming a hook and loop connection when engaged with corresponding hook-type engaging elements; and
   said hook and loop engaging layer end portions and said third hook and loop engaging inner layer portion of said second strap comprise hook-type engaging elements corresponding to said loop-type filamentary engaging elements.

6. A band for use securing and aligning medical tubing relative a portion of a human body, comprising:
   a first strap adjustably attachable to itself about a portion of a human body, said first strap having a hook and loop engaging inner layer portion and a first hook and loop engaging outer layer portion corresponding to said hook and loop engaging inner layer portion for receiving said hook and loop engaging inner layer portion attached thereon;
   said first strap having a second hook and loop engaging outer layer portion for receiving hook and loop attachments thereon; and
   a detachable second strap adjustably attachable along said second hook and loop engaging outer layer portion of said first strap;
   said second strap having a hook and loop engaging inner layer corresponding to said second hook and loop engaging outer layer portion of said first strap for attaching to said first strap at ends of said second strap, said hook and loop engaging inner layer being attached to a first foam substrate;
   said second strap being adapted to attach to said first strap across a portion of the medical tubing to secure and align the medical tubing against said first strap between said ends of said second strap.

7. The band of claim 6, wherein:
   said first hook and loop engaging outer layer portion is common with said second hook and loop engaging outer layer portion to define a common hook and loop engaging outer layer of said first strap; and
   said hook and loop engaging inner layer portion of said first strap corresponds to and adjustably attaches along said common hook and loop engaging outer layer, and said hook and loop engaging inner layer of said second strap corresponds to and adjustably attaches along said common hook and loop engaging outer layer.

8. The band of claim 7, wherein:
   said first strap includes a cotton-lined backing layer adhered to a second foam substrate, said cotton-lined backing layer comprising said common hook and loop engaging outer layer of said first strap; and said hook and loop engaging inner layer portion of said first strap is fastened to said second foam substrate at an end of said first strap.

9. The band of claim 8, wherein:
said second strap includes a cotton-lined backing layer adhered to said first foam substrate.

10. The band of claim 9, wherein:
said hook and loop engaging inner layer of said second strap is comprised of hook and loop engaging inner layer end portions fastened to said first foam substrate at ends of said second strap; and
said second strap attaches to said first strap at said hook and loop engaging inner layer end portions, a portion of said first foam substrate being exposed between said hook and loop engaging inner layer end portions and adapted for contacting and gripping across the medical tubing to further secure and align the medical tubing.

11. The band of claim 10, wherein:
said second strap includes a third hook and loop engaging inner layer portion fastened to said first foam substrate between said hook and loop engaging inner layer end portions of said second strap; and
said second strap being adapted to attach to said first strap at said third hook and loop engaging inner layer portion and across two medical tubing portions, one medical tubing portion being adapted to be secured between one of said ends of said second strap and said third hook and loop engaging inner layer portion, and the other medical tubing portion being adapted to be secured between said other end of said second strap and said third hook and loop engaging inner layer portion.

12. The band of claim 11, wherein:
said hook and loop engaging inner layer end portions and said third hook and loop engaging inner layer portion of said second strap and said hook and loop engaging inner layer portion of said first strap comprise hook-type engaging elements for attaching to said cotton-lined backing layer of said first strap.

* * * * *

UNITED STATES PATENT AND TRADEMARK OFFICE
CERTIFICATE OF CORRECTION

PATENT NO. : 5,244,464
DATED : September 14, 1993
INVENTOR(S) : Diane T. Madden, et al It is certified that error appears in the above-indentified patent and that said Letters Patent is hereby corrected as shown below:

Column 3, line 34, between the words "without" and "device" insert the following:
--requiring disconnection of the medical tubing for use with the--

Signed and Sealed this

Twenty-ninth Day of March, 1994

Attest:

BRUCE LEHMAN

Attesting Officer     Commissioner of Patents and Trademarks